United States Patent [19]
Hodgson et al.

[11] Patent Number: 6,077,677
[45] Date of Patent: Jun. 20, 2000

[54] FIBRONECTIN BINDING PROTEIN B COMPOUNDS

[75] Inventors: John Edward Hodgson, Malvern; Martin Karl Russell Burnham, Norristown, both of Pa.

[73] Assignee: SmithKline Beecham, p.l.c., United Kingdom

[21] Appl. No.: 09/205,049

[22] Filed: Dec. 4, 1998

Related U.S. Application Data

[62] Division of application No. 08/732,791, Oct. 15, 1996, Pat. No. 5,858,709.

[30] Foreign Application Priority Data

Oct. 16, 1995 [GB] United Kingdom .................... 9521146

[51] Int. Cl.$^7$ ................................................... G01N 33/53
[52] U.S. Cl. .......................... 435/7.1; 530/350; 536/23.1; 424/234.1
[58] Field of Search ........................ 530/350; 536/23.1; 435/7.1; 424/234.1

[56] References Cited

FOREIGN PATENT DOCUMENTS

WO/94 06830  3/1994  WIPO .

OTHER PUBLICATIONS

Jonsson et al. Euro. J. Biochem. 202: 1041–1048, 1991.
Sakata et al. Microb. Immunol. 38(5): 359–366, 1994.
Biochemistry 33: 6086–92 (1994) Fibronectin receptors from gram–positive bacteria: comparison of active sites.; H.J.Joh, K.House–Pompeo, J.M.Patti,S. Gurusiddappa & M.Hook.
Trends Biochem Sci 18: 136–40 (1993) Molecular evolution of bacterial cell–surface proteins. C.R.Goward, M.D.Scawen, J.P.Murphy & T.Atkinson.
Proc Natl Acad Sci U S A 86: 699–703 (1989) Nucleotide sequence of the gene for a fibronectin–binding protein from *Staphylococcus aureus*: use of this peptide sequence in the synthesis of biologically active peptides. C.Signas, G.Raucci, K.Jonsson, P.E. Lindgren, G.M. Anantharamaiah, M.Hook & M.Lindberg.

Microbiol Immunol 28: 863–71 (1984) Ability of various oral bacteria to bind human plasma fibronectin; S.Imai, N.Okahashi,T.Koga,T.Nisizawa & S.Hamada.

Infect Immun 41: 1261–8 (1983) Adherence of *streptococcus pyogenes, Escherichia coli*, and *Pseudomonas aeruginosa* to fibronectin–coated and uncoated epithelial cells. S.N.Abraham, E.H.Beachey & W.A.Simpson.

Vaudaux, et al., "Inhibition by Heparin and Derivatized Dextrans of *Staphylococcus Aureus* Adhesion to Fibronectin–coated Biomaterials", *J. Biomater. Sci. Polymer* Ed. vol. 4, No. 2: pp. 89–97, (1992).

Ryden, et al., "Detection of *Staphylococcus Aureus* Infection by Enzyme–Linked Immunosorbent Assay and Immunoblotting, Using High Molecular Weight Staphylococcal Proteins", *FEMS Microbiol. Immunol.*, vol. 2, No. 2: pp. 65–73, (1990).

*Primary Examiner*—Paula K. Hutzell
*Assistant Examiner*—Minh-Tam Davis
*Attorney, Agent, or Firm*—Edward R. Gimmi; Thomas S. Deibert; William T. King

[57] ABSTRACT

Novel fibronectin binding protein B polypeptides and DNA (RNA) encoding such novel fibronectin binding protein B and a procedure for producing such polypeptides by recombinant techniques is disclosed. Also disclosed are methods for utilizing such novel fibronectin binding protein B for the treatment of infection, particularly bacterial infections. Antagonists against such novel fibronectin binding protein B and their use as a therapeutic to treat infections, particularly bacterial infections are also disclosed. Also disclosed are diagnostic assays for detecting diseases related to the presence of novel fibronectin binding protein B nucleic acid sequences and the polypeptides in a host. Also disclosed are diagnostic assays for detecting polynucleotides encoding novel fibronectin binding protein B family and for detecting the polypeptide in a host.

13 Claims, 3 Drawing Sheets

Figure 1 [SEQ ID NO:1]

```
  1  SNGGYTLNLG DLDNSKDYVI KYEGEYDQNA KDLNFRTHLS GYHKYYPYYP
 51  YYPYYPVQLT WNNGVAFYSN NSKGDGKDKP NDPIIEKSEP IDLDIKSEPP
101  VEKHELTGTI EESNDSKPID FEYHTAVEGA EGHAEGIIET EEDSIHVDFE
151  ESTHENSKHH ADVVEYEEDT NPGGGQVTTE SNLVEL
```

Figure 2 [SEQ ID NO:2]

```
  1  AGTAATGGTG GGTACACATT GAACCCTGGC GATTAGATA ATTCGAAAGA
 51  CTATGTAATT AAATATGAAG GTGAATATGA TCAAAATGCT AAGGATCTAA
101  ATTCCGAAAC ACATCTTTCA GGATATCATA AATACTACCC ATACTATCCT
151  TATTACCCGT ATTATCCAGT TCAATTAACT TGGAACAACG GTGTTGCATT
201  TTACTCTAAT AATCCTAAAG GCGATGGTAA AGATAAACCA AATGATCCTA
251  TCATTGAGAA GAGTGAACCA ATTGATTTAG ACATTAAATC AGAGCCACCA
301  GTGGAGAAGC ATGAATTGAC TGGTACAATC GAAGAAAGTA ACGATTCTAA
351  GCCAATTGAT TTTGAATATC ATACAGCTGT TGAAGGTGCA GAAGGTCATG
401  CAGAAGGTAT TATTGAAACT GAAGAAGATT CTATTCATGT GGATTTTGAA
```

Figure 2a [SEQ ID NO:2]

451 GAATCTACAC ATGAAAATTC AAAACATCAC GCTGATGTTG TTGAATATGA

501 AGAGGATACA AACCCAGGTG GTGGCCAAGT AACAACTGAG TCTAACTTAG

551 TTGAATTA

FIBRONECTIN BINDING PROTEIN B COMPOUNDS

This is a divisional of application Ser. No. 08/732,791, filed Oct. 15, 1996, now U.S. Pat. No. 5,858,709.

SUMMARY OF THE INVENTION

The present invention relates to a novel cell surface protein from *S. aureus* WCUH 29, comprising the amino acid sequence given in SEQ ID NO:1, or a fragment, analogue or derivative thereof.

The invention also relates to a polypeptide fragment of the cell surface protein, having the amino acid sequence given in SEQ ID NO:1, or a derivative thereof.

In accordance with another aspect of the present invention, there are provided polynucleotides (DNA or RNA) which encode such polypeptides.

In particular the invention provides a polynucleotide having the DNA sequence given in SEQ ID NO:2.

The present invention also provides a novel protein from *Staphylococcus. aureus* WCUH29 obtainable by expression of a gene characterised in that it comprises the DNA sequence given SEQ ID NO:2, or a fragment, analogue or derivative thereof.

The present invention includes variants of the hereinabove described polynucleotides which encode fragments, analogs and derivatives of the polypeptide characterised by the deduced amino acid sequence of SEQ ID NO:1.

Further provided is a method for identifying compounds which bind to and inhibit an activity of the polypeptide of SEQ ID NO:1 comprising: contacting a cell expressing on the surface thereof a binding means for the polypeptide, said binding means being associated with a second component capable of providing a detectable signal in response to the binding of a compound to said binding means, with a compound to be screened under conditions to permit binding to the binding means; and determining whether the compound binds to and activates or inhibits the binding by detecting the presence or absence of a signal generated from the interaction of the compound with the binding means.

Also provided is an antibody against the polypeptide of SEQ ID NO:1. Still further provided is an antagonist which inhibits the activity of the polypeptide of SEQ ID NO:1.

A method is also provided for the treatment of an individual having need to inhibit the polypeptide of SEQ ID NO:1 comprising: administering to the individual a therapeutically effective amount of an antagonist against the polypeptide of the invention.

Provided is a process for diagnosing a disease related to expression of the polypeptide of the invention comprising- :determining a nucleic acid sequence encoding the polypeptide of SEQ ID NO:1.

A diagnostic process is provided comprising: analyzing for the presence of the polypeptide of SEQ ID NO:1 in a sample derived from a host.

Also provided is an antibody against the polypeptide of SEQ ID NO:1. Still further provided is an antagonist which inhibits the activity of the polypeptide of SEQ ID NO:1.

A method is also provided for the treatment of an individual having need to inhibit binding polypeptide of the invention comprising: administering to the individual a therapeutically effective amount of an antagonist against such polypeptide.

Provided is a process for diagnosing a disease related to expression of the polypeptide of the invention comprising- :determining a nucleic acid sequence encoding the polypeptide of SEQ ID NO:1.

A diagnostic process is provided comprising: analyzing for the presence of the polypeptide of SEQ ID NO:1 in a sample derived from a host.

The present invention also relates to vectors which include polynucleotides of the present invention, host cells which are genetically engineered with vectors of the invention and the production of polypeptides of the invention by recombinant techniques.

In accordance with yet a further aspect of the present invention, there is provided the use of a polypeptide of the invention for therapeutic or prophylactic purposes, for example, as an antibacterial agent or a vaccine.

In accordance with another aspect of the present invention, there is provided the use of a polynucleotide of the invention for therapeutic or prophylactic purposes, in particular genetic immunisation.

In accordance with yet another aspect of the present invention, there are provided inhibitors to such polypeptides, useful as antibacterial agents.

Another aspect of the invention is a pharmaceutical composition comprising the above polypeptide, polynucleotide or inhibitor of the invention and a pharmaceutically acceptable carrier.

In a particular aspect the invention provides the use of the polypeptide, polynucleotide or inhibitor of the invention to interfere with the immediate physical interaction between a pathogen and mammalian host responsible for sequelae of infection.

The invention further relates to the manufacture of a medicament for such uses.

This invention provides a method of screening drugs to identify those which interfere with the interaction of the cell surface protein or active fragment to mammalian cells.

BRIEF DESCRIPTION OF THE DRAWINGS

The following drawings depict certain embodiments of the invention. They are illustrative only and do not limit the invention otherwise disclosed herein.

FIG. 1 shows the polypeptide sequence of novel fibronectin binding protein B [SEQ ID NO:1].

FIG. 2 shows the polynucleotide sequence of novel fibronectin binding protein B [SEQ ID NO:2] deduced from the polynucleotide sequence of FIG. 1.

DETAILED DESCRIPTION OF THE INVENTION

The present invention relates to a novel cell surface protein from *S. aureus* WCUH 29, comprising the amino acid sequence given in SEQ ID NO:1, or a fragment, analogue or derivative thereof.

*Staphylococcus aureus* WCUH 29 has been deposited at the National Collection of Industrial and Marine Bacteria Ltd. (NCIMB), Aberdeen, Scotland under number NCIMB 40771 on Sep. 11, 1995.

The invention also relates to a polypeptide fragment of the cell surface protein, having the amino acid sequence given in SEQ ID NO:1, or a derivative thereof. The amino acid sequence of SEQ ID NO:1 displays 87% identity to Fibronectin Binding Protein B of *S. aureus* including the peptidoglycan spanning region.

Hereinafter the term polypeptide(s) will be used to refer to the cell surface protein, its fragments, analogues or derivatives as well as the polypeptide fragment or its derivatives.

In accordance with another aspect of the present invention, there are provided polynucleotides (DNA or RNA) which encode such polypeptides.

In particular the invention provides a polynucleotide having the DNA sequence given in SEQ ID NO:2. The invention further provides a polynucleotide encoding a cell surface protein from *S. aureus* WCUH 29 and characterised in that it comprises the DNA sequence given in SEQ ID NO:2.

The polynucleotide having the DNA sequence given in SEQ ID NO:2 was obtained from a library of clones of chromosomal DNA of *S. aureus* WCUH 29 in *E. coli*.

To obtain the polynucleotide encoding the cell surface protein using the DNA sequence given in SEQ ID NO:2 typically a library of clones of chromosomal DNA of *S. aureus* WCUH 29 in *E. coli* or some other suitable host is probed with a radiolabelled oligonucleotide, preferably a 17mer or longer, derived from the partial sequence. Clones carrying DNA identical to that of the probe can then be distinguished using high stringency washes. By sequencing the individual clones thus identified with sequencing primers designed from the original sequence it is then possible to extend the sequence in both directions to determine the full gene sequence. Conveniently such sequencing is performed using denatured double stranded DNA prepared from a plasmid clone. Suitable techniques are described by Maniatis, T., Fritsch, E. F. and Sambrook, J. in MOLECULAR CLONING, A Laboratory Manual [2nd edition 1989 Cold Spring Harbor Laboratory. see Screening By Hybridization 1.90 and Sequencing Denatured Double-Stranded DNA Templates 13.70].

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the polypeptide may be identical to the coding sequence shown in SEQ ID NO:2 or may be a different coding sequence which coding sequence, as a result of the redundancy or degeneracy of the genetic code, encodes the same polypeptide.

The present invention includes variants of the hereinabove described polynucleotides which encode fragments, analogs and derivatives of the polypeptide characterised by the deduced amino acid sequence of SEQ ID NO:1. The variant of the polynucleotide may be a naturally occurring allelic variant of the polynucleotide or a non-naturally occurring variant of the polynucleotide.

Thus, the present invention includes polynucleotides encoding the same polypeptide characterised by the deduced amino acid sequence of SEQ ID NO:1 as well as variants of such polynucleotides which variants encode for a fragment, derivative or analog of the polypeptide. Such nucleotide variants include deletion variants, substitution variants and addition or insertion variants.

The polynucleotide may have a coding sequence which is a naturally occurring allelic variant of the coding sequence characterised by the DNA sequence of SEQ ID NO:2. As known in the art, an allelic variant is an alternate form of a polynucleotide sequence which may have a substitution, deletion or addition of one or more nucleotides, which does not substantially alter the function of the encoded polypeptide.

The polynucleotide which encodes for the mature polypeptide, i.e. the native cell surface protein, may include only the coding sequence for the mature polypeptide or the coding sequence for the mature polypeptide and additional coding sequence such as a leader or secretory sequence or a proprotein sequence.

Thus, the term "polynucleotide encoding a polypeptide" encompasses a polynucleotide which includes only coding sequence for the polypeptide as well as a polynucleotide which includes additional coding and/or non-coding sequence.

The present invention therefore includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence at either the 5' or 3' terminus of the gene which allows for purification of the polypeptide of the present invention. The marker sequence may be a hexa-histidine tag supplied by the pQE series of vectors (supplied commercially by Quiagen Inc.) to provide for purification of the polypeptide fused to the marker in the case of a bacterial host. The present invention further relates to polynucleotides which hybridize to the hereinabove-described sequences if there is at least 50% and preferably at least 70% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the polypeptide characterised by the deduced amino acid sequence of SEQ ID NO:1. The invention also provides an isolated polynucleotide comprising a member selected from the group consisting of: a polynucleotide having at least a 70% identity to a polynucleotide encoding a polypeptide comprising amino acids of SEQ ID NO:1; a polynucleotide which is complementary to the polynucleotide of (a); and a polynucleotide comprising at least 15 sequential bases of the polynucleotide of (a) or (b).

The deposit referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. § 112. The sequence of the polynucleotides contained in the deposited material, as well as the amino acid sequence of the polypeptides encoded thereby, are incorporated herein by reference and are controlling in the event of any-conflict with any description of sequences herein. A license may be required to make, use or sell the deposited material, and no such license is hereby granted.

The terms "fragment," "derivative" and "analog" when referring to the polypeptide characterised by the deduced amino acid sequence of SEQ ID NO:1, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide characterised by the deduced amino acid sequence of SEQ ID NO:1 may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the polypeptide is fused with another compound, such as a compound to increase the half-life of the polypeptide (for example, polyethylene glycol), or (iv) one in which the additional amino acids are fused to the polypeptide, such as a leader or secretory sequence or a sequence which is employed for purification of the polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

In accordance with yet a further aspect of the present invention, there is therefore provided a process for producing the polypeptide of the invention by recombinant techniques by expressing a polynucleotide encoding said polypeptide in a host and recovering the expressed product. Alternatively, the polypeptides of the invention can be synthetically produced by conventional peptide synthesizers.

Host cells are genetically engineered (transduced or transformed or transfected) with the vectors of this invention which may be, for example, a cloning vector or an expression vector. The vector may be, for example, in the form of a plasmid, a cosmid, a phage, etc. The engineered host cells can be cultured in conventional nutrient media modified as appropriate for activating promoters, selecting transformants or amplifying the genes. The culture conditions, such as temperature, pH and the like, are those previously used with the host cell selected for expression, and will be apparent to the ordinarily skilled artisan.

Suitable expression vectors include chromosomal, non-chromosomal and synthetic DNA sequences, e.g., bacterial plasmids; phage DNA; baculovirus; yeast plasmids; vectors derived from combinations of plasmids and phage DNA. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art.

The DNA sequence in the expression vector is operatively linked to an appropriate expression control sequence(s) (promoter) to direct MRNA synthesis. As representative examples of such promoters, there may be mentioned: LTR or SV40 promoter, the E. coli. lac or trp, the phage lambda $P_L$ promoter and other promoters known to control expression of genes in eukaryotic or prokaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence may or may not contain a signal peptide or leader sequence. The polypeptides of the present invention can be expressed using, for example, the E. coli tac promoter or the protein A gene (spa) promoter and signal sequence. Leader sequences can be removed by the bacterial host in post-translational processing. See, e.g., U.S. Pat. Nos. 4,431,739; 4,425,437; 4,338,397. Promoter regions can be selected from any desired gene using CAT (chloramphenicol transferase) vectors or other vectors with selectable markers. Two appropriate vectors are PKK232-8 and PCM7. Particular named bacterial promoters include lac, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In addition to control sequences, it may be desirable to add regulatory sequences which allow for regulation of the expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the coding sequences may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

The vector containing the appropriate DNA sequence as hereinabove described, as well as an appropriate promoter or control sequence, may be employed to transform an appropriate host to permit the host to express the protein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pET-3 vectors (Stratagene), pQE70, pQE60, pQE-9 (Qiagen), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pBlueBacHI (Invitrogen), pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Examples of recombinant DNA vectors for cloning and host cells which they can transform include the bacteriophage 1 (E. coli), pBR322 (E. coli), pACYC177 (E. coli), pKT230 (gram-negative bacteria), pGV1 106 (gram-negative bacteria), pLAFR1 (gram-negative bacteria), pME290 (non-E. coli gram-negative bacteria), pHV 14 (E. coli and Bacillus subtilis), pBD9 (Bacillus), pIJ61 (Streptomyces), pUC6 (Streptomyces), YIp5 (Saccharomyces), a baculovirus insect cell system, YCp 19 (Saccharomyces). See, generally, "DNA Cloning": Vols. I & II, Glover et al. ed. IRL Press Oxford (1985) (1987) and; T. Maniatis et al. ("Molecular Cloning" Cold Spring Harbor Laboratory (1982).

In some cases, it may be desirable to add sequences which cause the secretion of the polypeptide from the host organism, with subsequent cleavage of the secretory signal.

Polypeptides can be expressed in host cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Depending on the expression system and host selected, the polypeptide of the present invention may be produced by growing host cells transformed by an expression vector described above under conditions whereby the polypeptide of interest is expressed. The polypeptide is then isolated from the host cells and purified. If the expression system secretes the polypeptide into growth media, the polypeptide can be purified directly from the media. If the polypeptide is not secreted, it is isolated from cell lysates or recovered from the cell membrane fraction. Where the polypeptide is localized to the cell surface, whole cells or isolated membranes can be used as an assayable source of the desired gene product. Polypeptide expressed in bacterial hosts such as E. coli may require isolation from inclusion bodies and refolding. Where the mature protein has a very hydroophobic region (normally at the C-terminus) which leads to an insoluble product of overexpression, it may be desirable to express a truncated protein in which the hydrophobic region has been deleted. The selection of the appropriate growth conditions and recovery methods are within the skill of the art.

The polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography hydroxylapatite chromatography and lectin chromatography. Protein refolding steps can be used, as necessary, in completing configuration of the mature protein. Finally, high performance liquid chromatography (HPLC) can be employed for final purification steps.

Depending upon the host employed in a recombinant production procedure, the polypeptides of the present invention may be glycosylated or may be non-glycosylated. Polypeptides of the invention may also include an initial methionine amino acid residue.

A "replicon" is any genetic element (e.g., plasmid, chromosome, virus) that functions as an autonomous unit of DNA replication in vivo; i.e., capable of replication under its own control.

A "vector" is a replicon, such as a plasmid, phage, or cosmid, to which another DNA segment may be attached so as to bring about the replication of the attached segment.

A "double-stranded DNA molecule" refers to the polymeric form of deoxyribonucleotides (bases adenine, guanine, thymine, or cytosine) in a double-stranded helix, both relaxed and supercoiled. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having the sequence homologous to the mRNA).

A DNA "coding sequence of" or a "nucleotide sequence encoding" a particular protein, is a DNA sequence which is transcribed and translated into a polypeptide when placed under the control of appropriate regulatory sequences.

A "promoter sequence" is a DNA regulatory region capable of binding RNA polymerase in a cell and initiating transcription of a downstream (3' direction) coding sequence. For purposes of defining the present invention, the promoter sequence is bound at the 3' terminus by a translation start codon (e.g., ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

DNA "control sequences" refers collectively to promoter sequences, ribosome binding sites, polyadenylation signals, transcription termination sequences, upstream regulatory domains, enhancers, and the like, which collectively provide for the expression (i.e., the transcription and translation) of a coding sequence in a host cell.

A control sequence "directs the expression" of a coding sequence in a cell when RNA polymerase will bind the promoter sequence and transcribe the coding sequence into mRNA, which is then translated into the polypeptide encoded by the coding sequence.

A "host cell" is a cell which has been transformed or transfected, or is capable of transformation or transfection by an exogenous DNA sequence.

A cell has been "transformed" by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to eukaryotic cells, a stably transformed or transfected cell is one in which the exogenous DNA has become integrated into the chromosome so that it is inherited by daughter cells through chromosome replication. This stability is demonstrated by the ability of the eukaryotic cell to establish cell lines or clones comprised of a population of daughter cell containing the exogenous DNA.

A "clone" is a population of cells derived from a single cell or common ancestor by mitosis. A "cell line" is a clone of a primary cell that is capable of stable growth in vitro for many generations.

A "heterologous" region of a DNA construct is an identifiable segment of DNA within or attached to another DNA molecule that is not found in association with the other molecule in nature.

In accordance with yet a further aspect of the present invention, there is provided the use of a polypeptide of the invention for therapeutic or prophylactic purposes, for example, as an antibacterial agent or a vaccine.

In accordance with another aspect of the present invention, there is provided the use of a polynucleotide of the invention for therapeutic or prophylactic purposes, in particular genetic immunisation.

In accordance with yet another aspect of the present invention, there are provided inhibitors to such polypeptides, useful as antibacterial agents. In particular, there are provided antibodies against such polypeptides.

Another aspect of the invention is a pharmaceutical composition comprising the above polypeptide, polynucleotide or inhibitor of the invention and a pharmaceutically acceptable carrier.

In a particular aspect the invention provides the use of the polypeptide, polynucleotide or inhibitor of the invention to interfere with the immediate physical interaction between a pathogen and mammalian host responsible for sequelae of infection. In particular the molecules of the invention may be used:

i) in the prevention of adhesion of bacteria, in particular gram positive bacteria, to mammalian extracellular matrix proteins on in-dwelling devices or to extracellular matrix proteins in wounds;

ii) to block cell surface protein mediated mammalian cell invasion by, for example, initiating phosphorylation of mammalian tyrosine kinases (Rosenshine et al. [1992] Infect. Immun. 60, 2211–7)

iii) to block bacterial adhesion between mammalian extracellular matrix proteins and bacterial cell surface proteins which mediate tissue damage iv) to block the normal progression of pathogenesis in infections initiated other than by the implantation of in-dwelling devices or by other surgical techniques.

The invention further relates to the manufacture of a medicament for such uses.

The polypeptide may be used as an antigen for vaccination of a host to produce specific antibodies which protect against invasion of bacteria, for example by blocking adherence of bacteria to damaged tissue. Examples of tissue damage include wounds in skin or connective tissue caused e.g. by mechanical, chemical or thermal damage or by implantation of indwelling devices, or wounds in the mucous membranes, such as the mouth, mammary glands, urethra or vagina.

The polypeptides or cells expressing them can be used as an immunogen to produce antibodies thereto. These antibodies can be, for example, polyclonal or monoclonal antibodies. The term antibodies also includes chimeric, single chain, and humanized antibodies, as well as Fab fragments, or the product of an Fab expression library. Various procedures known in the art may be used for the production of such antibodies and fragments.

Antibodies generated against the polypeptides of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

Polypeptide derivatives include antigenically or immunologically equivalent derivatives which form a particular aspect of this invention.

The term 'antigenically equivalent derivative' as used herein encompasses a polypeptide or its equivalent which will be specifically recognised by certain antibodies which, when raised to the protein or polypeptide according to the present invention, interfere with the immediate physical interaction between pathogen and mammalian host.

The term 'immunologically equivalent derivative' as used herein encompasses a peptide or its equivalent which when used in a suitable formulation to raise antibodies in a vertebrate, the antibodies act to interfere with the immediate physical interaction between pathogen and mammalian host.

In particular derivatives which are slightly longer or slightly shorter than the native cell surface protein or polypeptide fragment of the present invention may be used. In addition, polypeptides in which one or more of the amino acid residues are modified may be used. Such peptides may, for example, be prepared by substitution, addition, or rearrangement of amino acids or by chemical modification thereof. All such substitutions and modifications are generally well known to those skilled in the art of peptide chemistry.

The N-terminal fragment of the protein, i.e. not in the cytoplasm, is most relevant for the preparation of antibodies to the regions of proteins (see—Binding and activation of plasminogen at the surface of *Staphylococus aureus* Kuusela, P and Saksela, O. [1990] Eur. J. Biochem 193: 759–65).

The polypeptide, such as an antigenically or immunologically equivalent derivative or a fusion protein thereof is used as an antigen to immunize a mouse or other animal such as a rat or chicken. The fusion protein may provide stability to the polypeptide. The antigen may be associated, for example by conjugation, with an immunogenic carrier protein for example bovine serum albumin (BSA) or keyhole limpet haemocyanin (KLH). Alternatively a multiple antigenic peptide comprising multiple copies of the the protein or polypeptide, or an antigenically or immunologically equivalent polypeptide thereof may be sufficiently antigenic to improve immunogenicity so as to obviate the use of a carrier.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention.

Using the procedure of Kohler and Milstein (1975 Nature 256, 495–497), antibody-containing cells from the immunised mammal are fused with myeloma cells to create hybridoma cells secreting monoclonal antibodies.

The hybridomas are screened to select a cell line with high binding affinity and favorable cross reaction with other staphylococcal species using one or more of the original polypeptide and/or the fusion protein. The selected cell line is cultured to obtain the desired Mab.

Hybridoma cell lines secreting the monoclonal antibody are another aspect of this invention.

Alternatively phage display technology could be utilised to select antibody genes with binding activities towards the polypeptide either from repertoires of PCR amplified v-genes of lymphocytes from humans screened for possessing anti-Fbp or from naive libraries (McCafferty, J. et al., (1990), Nature 348, 552–554; Marks, J. et al., (1992) Biotechnology 10, 779–783). The affinity of these antibodies can also be improved by chain shuffling (Clackson, T. et al., (1991) Nature 352, 624–628).

The antibody should be screened again for high affinity to the polypeptide and/or fusion protein.

As mentioned above, a fragment of the final antibody may be prepared.

The antibody may be either intact antibody of $M_r$ approx 150,000 or a derivative of it, for example a Fab fragment or a Fv fragment as described in Skerra, A and Pluckthun, A (1988) Science 240 1038–1040. If two antigen binding domains are present each domain may be directed against a different epitope—termed 'bispecific' antibodies.

The antibody of the invention may be prepared by conventional means for example by established monoclonal antibody technology (Kohler, G. and Milstein, C. (1975) , Nature, 256, 495–497) or using recombinant means e.g. combinatorial libraries, for example as described in Huse, W. D. et al., (1989) Science 246,1275–1281.

Preferably the antibody is prepared by expression of a DNA polymer encoding said antibody in an appropriate expression system such as described above for the expression of polypeptides of the invention. The choice of vector for the expression system will be determined in part by the host, which may be a prokaryotic cell, such as *E. coli* (preferably strain B) or Streptomyces sp. or a eukaryotic cell, such as a mouse C127, mouse myeloma, human HeLa, Chinese hamster ovary, filamentous or unicellular fungi or insect cell. The host may also be a transgenic animal or a transgenic plant [for example as described in Hiatt, A et al., (1989) Nature 34, 76–78]. Suitable vectors include plasmids, bacteriophages, cosmids and recombinant viruses, derived from, for example, baculoviruses and vaccinia.

The Fab fragment may also be prepared from its parent monoclonal antibody by enzyme treatment, for example using papain to cleave the Fab portion from the Fc portion.

Preferably the antibody or derivative thereof is modified to make it less immunogenic in the patient. For example, if the patient is human the antibody may most preferably be 'humanised'; where the complimentarily determining region (s) of the hybridoma-derived antibody has been transplanted into a human monoclonal antibody , for example as described in Jones, P. et al (1986), Nature 321, 522–525 or Tempest et al.,(1991) Biotechnology 9, 266–273.

The modification need not be restricted to one of 'humanisation'; other primate sequences (for example Newman, R. et al .1992, Biotechnology,10, 1455–1460) may also be used.

The humanised monoclonal antibody, or its fragment having binding activity, form a particular aspect of this invention.

This invention provides a method of screening drugs to identify those which interfere with the interaction of the cell surface protein or active fragment to mammalian cells, the method comprising incubating a mammalian cell or membrane preparation with labeled polypeptide in the presence of the drug and measuring the ability of the drug to block this interaction.

The use of a polynucleotide of the invention in genetic immunisation will preferably employ a suitable delivery method such as direct injection of plasmid DNA into muscles (Wolff et al., Hum Mol Genet 1992, 1:363, Manthorpe et al., Hum. Gene Ther. 1963:4, 419), delivery of DNA complexed with specific protein carriers ( Wu et al., J Biol Chem 1989:264,16985), coprecipitation of DNA with calcium phosphate (Benvenisty & Reshef, PNAS, 1986:83, 9551), encapsulation of DNA in various forms of liposomes (Kaneda et al., Science 1989:243,375), particle bombardment (Tang et al., Nature 1992, 356:152, Eisenbraun et al., DNA Cell Biol 1993, 12:791) and in vivo infection using cloned retroviral vectors (Seeger et al, PNAS 1984:81, 5849). Suitable promoters for muscle transfection include CMV, RSV, SRa, actin, MCK, alpha globin, adenovirus and dihydrofolate reductase.

In therapy or as a prophylactic, the active agent may be administered to a patient as an injectable composition, for example as a sterile aqueous dispersion, preferably isotonic.

Alternatively the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration to human patients, it is expected that the daily dosage level of the active agent will be from 0.01 to 10 mg/kg, typically around 1 mg/kg. The physician in any event will determine the actual dosage which will be most suitable for an individual patient and will vary with the age, weight and response of the particular patient. The above dosages are exemplary of the average case. There can, of course, be individual instances where higher or lower dosage ranges are merited, and such are within the scope of this invention.

In-dwelling devices include surgical implants, prosthetic devices and catheters, i.e., devices that are introduced to the body of a patient and remain in position for an extended time. Such devices include, for example, artificial joints, heart valves, pacemakers, vascular grafts, vascular catheters, cerebrospinal fluid shunts, urinary catheters, continuous ambulatory peritoneal dialysis (CAPD) catheters, etc.

The composition of the invention may be administered by injection to achieve a systemic effect against relevant bacteria shortly before insertion of an in-dwelling device. Treatment may be continued after surgery during the in-body time of the device. In addition, the composition could also be used to broaden perioperative cover for any surgical technique to prevent staphylococcal wound infections.

Many orthopaedic surgeons consider that patients with prosthetic joints should be considered for antibiotic prophylaxis before dental treatment that could produce a bacteraemia. Late deep infection is a serious complication sometimes leading to loss of the prosthetic joint and is accompanied by significant morbidity and mortality. It may therefore be possible to extend the use of the active agent as a replacement for prophylactic antibiotics in this situation.

In addition to the therapy described above, the compositions of this invention may be used generally as a wound treatment agent to prevent adhesion of bacteria to matrix proteins exposed in wound tissue and for prophylactic use in dental treatment as an alternative to, or in conjunction with, antibiotic prophylaxis.

Alternatively, the composition of the invention may be used to bathe an indwelling device immediately before insertion. The active agent will preferably be present at a concentration of 1 µg/ml to 10 mg/ml for bathing of wounds or indwelling devices.

A vaccine composition is conveniently in injectable form. Conventional adjuvants may be employed to enhance the immune response.

A suitable unit dose for vaccination is 0.5–5 ug/kg of antigen, and such dose is preferably administered 1–3 times and with an interval of 1–3 weeks.

With the indicated dose range, no adverse toxicological effects will be observed with the compounds of the invention which would preclude their administration to suitable patients.

The antibodies described above may also be used as diagnostic reagents to detect the presence of bacteria containing the cell surface protein.

In order to facilitate understanding of the following example certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37 C are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 µg of approximately equimolar amounts of the DNA fragments to be ligated.

EXAMPLE 1

Isolation of DNA coding for Novel Cell Surface Protein from *S. Aureus* WCUH 29

The polynucleotide having the DNA sequence given in SEQ D NO:2 was obtained from a library of clones of chromosomal DNA of *S. aureus* WCUH 29 in *E. coli*. Libraries may be prepared by routine methods, for example:

Methods 1 and 2

Total cellular DNA is isolated from *Staphylococcus aureus* strain WCUH29 (NCIMB 40771) according to standard procedures and size-fractionated by either of two methods.

Method 1

Total cellular DNA is mechanically sheared by passage through a needle in order to size-fractionate according to standard procedures. DNA fragments of up to 11 kbp in size are rendered blunt by treatment with exonuclease and DNA polymerase, and EcoRI linkers added. Fragments are ligated into the vector Lambda ZapII that has been cut with EcoRI, the library packaged by standard procedures and *E. coli* infected with the packaged library. The library is amplified by standard procedures.

Method 2

Total cellular DNA is partially hydrolsed with a combination of four restriction enzymes (RsaI, PalI, AluI and Bshl235I) and size-fractionated according to standard procedures. EcoRI linkers are ligated to the DNA and the fragments then ligated into the vector Lambda ZapII that have been cut with EcoRI, the library packaged by standard procedures, and *E. coli* infected with the packaged library. The library is amplified by standard procedures.

What is claimed is:

1. An isolated protein comprising a polypeptide comprising SEQ ID NO:1.

2. A composition comprising the isolated protein of claim 1 and a pharmaceutically acceptable carrier.

3. An isolated fusion protein comprising a heterologous amino acid sequence fused to the polypeptide of claim 1.

4. A composition comprising the isolated fusion protein of claim 3 and a pharmaceutically acceptable carrier.

5. The isolated protein of claim 1, wherein the isolated protein consists of the amino acid sequence set forth in SEQ ID NO:1.

6. A composition comprising the isolated protein of claim 5 and a pharmaceutically acceptable carrier.

7. An isolated protein comprising a polypeptide, wherein the polypeptide comprises an amino acid sequence selected from the group consisting of:
    (a) SEQ ID NO:1; and,
    (b) an amino acid sequence identical to SEQ ID NO:1 except that, over the entire length corresponding to SEQ ID NO:1, the amino acid sequence has a substitution, deletion or insertion of one amino acid.

8. A composition comprising the isolated protein of claim 7 and a pharmaceutically acceptable carrier.

9. An isolated fusion protein comprising a heterologous amino acid sequence fused to the polypeptide of claim 7.

10. A composition comprising the isolated fusion protein of claim 9 and a pharmaceutically acceptable carrier.

11. The isolated protein of claim 7, wherein the isolated protein consists of the polypeptide, wherein the polypeptide consists of the amino acid sequence selected from the group consisting of:
    (a) SEQ ID NO:1; and,
    (b) an amino acid sequence identical to SEQ ID NO:1 except that, over the entire length corresponding to SEQ ID NO:1, the amino acid sequence has a substitution, deletion or insertion of one amino acid.

12. A composition comprising the isolated protein of claim 11 and a pharmaceutically acceptable carrier.

13. A method for producing antibodies in a mammal comprising: delivering to a tissue of the mammal the isolated protein of claim 1, wherein the protein is effective to induce an immunological response to the amino acid sequence set forth in SEQ ID NO:1; and, wherein the polypeptide induces an immunological response to produce antibodies to the amino acid sequence set forth in SEQ ID NO:1.

* * * * *

```
                          SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 186 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:1:

Ser Asn Gly Gly Tyr Thr Leu Asn Leu Gly Asp Leu Asp Asn Ser Lys
1               5                   10                  15

Asp Tyr Val Ile Lys Tyr Glu Gly Glu Tyr Asp Gln Asn Ala Lys Asp
            20                  25                  30

Leu Asn Phe Arg Thr His Leu Ser Gly Tyr His Lys Tyr Tyr Pro Tyr
            35                  40                  45

Tyr Pro Tyr Tyr Pro Tyr Tyr Pro Val Gln Leu Thr Trp Asn Asn Gly
    50                  55                  60

Val Ala Phe Tyr Ser Asn Asn Ser Lys Gly Asp Gly Lys Asp Lys Pro
65              70                  75                  80

Asn Asp Pro Ile Ile Glu Lys Ser Glu Pro Ile Asp Leu Asp Ile Lys
                85                  90                  95

Ser Glu Pro Pro Val Glu Lys His Glu Leu Thr Gly Thr Ile Glu Glu
            100                 105                 110

Ser Asn Asp Ser Lys Pro Ile Asp Phe Glu Tyr His Thr Ala Val Glu
            115                 120                 125

Gly Ala Glu Gly His Ala Glu Gly Ile Ile Glu Thr Glu Glu Asp Ser
        130                 135                 140

Ile His Val Asp Phe Glu Glu Ser Thr His Glu Asn Ser Lys His His
145                 150                 155                 160

Ala Asp Val Val Glu Tyr Glu Glu Asp Thr Asn Pro Gly Gly Gly Gln
                165                 170                 175
```

```
Val Thr Thr Glu Ser Asn Leu Val Glu Leu
        180                 185
```

(2) INFORMATION FOR SEQ ID NO:2:

(i) SEQUENCE CHARACTERISTICS:
        (A) LENGTH: 558 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:2:

```
AGTAATGGTG GGTACACATT GAACCTTGGC GATTTAGATA ATTCGAAAGA CTATGTAATT      60

AAATATGAAG GTGAATATGA TCAAAATGCT AAGGATCTAA ATTTCCGAAC ACATCTTTCA     120

GGATATCATA AATACTACCC ATACTATCCT TATTACCCGT ATTATCCAGT TCAATTAACT     180

TGGAACAACG GTGTTGCATT TTACTCTAAT AATCCTAAAG GCGATGGTAA AGATAAACCA     240

AATGATCCTA TCATTGAGAA GAGTGAACCA ATTGATTTAG ACATTAAATC AGAGCCACCA     300

GTGGAGAAGC ATGAATTGAC TGGTACAATC GAAGAAAGTA ACGATTCTAA GCCAATTGAT     360

TTTGAATATC ATACAGCTGT TGAAGGTGCA GAAGGTCATG CAGAAGGTAT TATTGAAACT     420

GAAGAAGATT CTATTCATGT GGATTTTGAA GAATCTACAC ATGAAAATTC AAAACATCAC     480

GCTGATGTTG TTGAATATGA AGAGGATACA AACCCAGGTG GTGGCCAAGT AACAACTGAG     540

TCTAACTTAG TTGAATTA                                                   558
```